(12) United States Patent
Petersen et al.

(10) Patent No.: US 9,327,113 B2
(45) Date of Patent: May 3, 2016

(54) ACTIVE FIXATION LEAD HAVING A ROTATABLE CURVE

(71) Applicant: Cardiac Pacemakers, Inc., St. Paul, MN (US)

(72) Inventors: Eric M. Petersen, Maple Grove, MN (US); Todd Rowe, Excelsior, MN (US); Rui He, Buffalo Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 189 days.

(21) Appl. No.: 14/096,704

(22) Filed: Dec. 4, 2013

(65) Prior Publication Data

US 2014/0155974 A1    Jun. 5, 2014

Related U.S. Application Data

(60) Provisional application No. 61/733,524, filed on Dec. 5, 2012.

(51) Int. Cl.
*A61N 1/05* (2006.01)
*A61N 1/375* (2006.01)

(52) U.S. Cl.
CPC .............. *A61N 1/059* (2013.01); *A61N 1/0573* (2013.01); *A61N 1/3752* (2013.01); *A61N 1/056* (2013.01)

(58) Field of Classification Search
CPC ..... A61N 1/0488; A61N 1/056; A61N 1/057; A61N 1/059; A61N 1/3752; A61N 1/0573
USPC ................................. 607/119, 122, 126, 116

See application file for complete search history.

(56) References Cited

U.S. PATENT DOCUMENTS 6,141,593 A * 10/2000 Patag ............................ 607/122
6,212,434 B1     4/2001 Scheiner et al.
(Continued)

FOREIGN PATENT DOCUMENTS

EP            0180348 B1     5/1986

OTHER PUBLICATIONS

International Search Report and Written Opinion issued in PCT/US2013/073103, mailed Feb. 25, 2014, 9 pages.

(Continued)

*Primary Examiner* — Theodore Stigell
*Assistant Examiner* — Michael Carey
(74) *Attorney, Agent, or Firm* — Faegre Baker Daniels LLP (57) ABSTRACT

Various embodiments concern a lead having a proximal section and a curbed section. The lead can comprise an outer tubular portion having a bias such that the lead assumes a curved shape along the curved section. The lead can further include an inner tubular portion extending within the outer tubular portion, the inner tubular portion comprising an inner coil conductor and an inner polymer jacket over the inner coil conductor along the curved section, the inner tubular member stiffer along the proximal section than the curved section, the outer tubular portion stiffer along the curved section relative to the inner tubular portion along the curved section such that the inner tubular portion can rotate relative to the outer tubular portion while the curved shape is substantially maintained. Relative rotation can extend and rotate and active fixation element.

20 Claims, 5 Drawing Sheets

(56) References Cited

U.S. PATENT DOCUMENTS

| | | |
|---|---|---|
| 6,463,334 B1 | 10/2002 | Flynn et al. |
| 7,558,632 B1 * | 7/2009 | Salys .......................... 607/125 |
| 8,494,651 B2 | 7/2013 | Hearer et al. |
| 2007/0299493 A1 | 12/2007 | Osypka |
| 2011/0093053 A1 * | 4/2011 | Djurling ................ A61N 1/056 607/116 |
| 2011/0160825 A1 | 6/2011 | Haarer et al. |

OTHER PUBLICATIONS

International Preliminary Examination Report issued in PCT/US2013/073103, completed Jun. 9, 2015, 7 pages.

* cited by examiner

ACTIVE FIXATION LEAD HAVING A ROTATABLE CURVE

CROSS-REFERENCE TO RELATED APPLICATION

This application claims priority to U.S. Provisional Application 61/733,524, filed Dec. 5, 2012, which is herein incorporated by reference in its entirety.

TECHNICAL FIELD

The present disclosure relates generally to implantable medical leads. More specifically, the disclosure relates to leads having biased shapes.

BACKGROUND

When functioning properly, the human heart maintains its own intrinsic rhythm and is capable of pumping adequate blood throughout the body's circulatory system. However, some individuals have irregular cardiac rhythms, referred to as cardiac arrhythmias, which can result in diminished blood circulation and cardiac output. One manner of treating cardiac arrhythmias includes the use of a pulse generator (PG) such as a pacemaker, an implantable cardioverter defibrillator (ICD), or a cardiac resynchronization (CRT) device. Such devices are typically coupled to one or more implantable leads having one or more electrodes that can be used to deliver pacing therapy and/or electrical shocks to the heart. Implantable leads can additionally or alternatively be used to stimulate other nervous and/or musculature systems of the body.

SUMMARY

Example 1 concerns an implantable lead having a proximal section, a distal section, and a curved section between the proximal section and the distal section, the implantable lead comprising: an outer tubular portion extending from the proximal section to the distal section, the outer tubular portion defining an exterior surface of the implantable lead, the outer tubular portion having a bias such that the implantable lead assumes a curved shape along the curved section; an inner tubular portion extending within the outer tubular portion, the inner tubular portion comprising an inner coil conductor and an inner polymer jacket over the inner coil conductor along the curved section, the inner coil conductor extending from the proximal section to the distal section and having a steeper filar pitch along the curved section than along the proximal section, the inner polymer jacket having a plurality of slots along the curved section that increases the flexibility of the inner tubular portion; and an active fixation element on the distal end, the active fixation element in electrical connection with the inner coil conductor, the active fixation element configured to affix to tissue by rotation of the inner tubular portion relative to the outer tubular member.

In example 2, the lead of example 1, wherein the outer tubular portion is stiffer than the inner tubular portion along the curved section such that the curved shape of the implantable lead is substantially maintained during rotation of the inner tubular portion relative to the outer tubular portion.

In example 3, the lead of either of examples 1 or 2, wherein the inner tubular portion is relatively stiffer along the proximal section and less stiff along the curved portion.

In example 4, the lead of any of examples 1-3, wherein the inner polymer jacket inhibits radial expansion of the inner coil conductor during rotation of the inner tubular portion.

In example 5, the lead of any of examples 1-4, wherein the inner coil conductor has the same filar pitch along the proximal section and the distal section.

In example 6, the lead of any of example 1-5, the inner tubular portion comprises a polymer coating on the inner coil conductor along the proximal section, the polymer coating does not extend along the curved section, and the inner polymer jacket does not extend over the inner coil conductor along the proximal section.

In example 7, the lead of any of examples 1-6, wherein the inner polymer jacket does not extend along the distal section.

In example 8, the lead of any of examples 1-7, wherein the inner polymer jacket is a tube and the inner coil conductor can move within the tube.

In example 9, the lead of any of examples 1-8, wherein the inner coil conductor is a unifilar coil.

In example 10, the lead of any of examples 1-9, further comprising an active fixation mechanism, the active fixation mechanism comprising a housing, an inner coupling located within the housing, and the active fixation element, the housing and the inner coupling having complementary threading and being rotatable relative to each other, the inner coupling connected to the inner tubular portion and the active fixation element, the housing connected to the outer tubular portion, the active fixation mechanism configured such that rotation of the inner tubular portion relative to the outer tubular portion extends and rotates the active fixation element for tissue fixation.

In example 11, the lead of any of examples 1-10, further comprising a proximal connector configured to interface with an implantable pulse generator, the proximal connector comprising a mechanism that can rotate the inner tubular portion relative to the outer tubular portion, wherein the inner tubular portion and the outer tubular portion are each connected to the proximal connector.

In example 12, the lead of any of examples 1-11, wherein the outer portion further comprises a ring electrode and an outer coil conductor, the outer coil conductor electrically connecting with the ring electrode.

Example 13 concerns an implantable lead having a proximal section, a distal section, and a curved section between the proximal section and the distal section, the implantable lead comprising: an outer tubular portion extending from the proximal section to the distal section, the outer tubular portion defining an exterior surface of the implantable lead, the outer tubular portion having a bias such that the implantable lead assumes a curved shape along the curved section; an inner tubular portion extending within the outer tubular portion, the inner tubular portion comprising an inner coil conductor and an inner polymer jacket over the inner coil conductor along the curved section, the inner coil conductor extending from the proximal section to the distal section, the inner polymer jacket having a plurality of slots along the curved section that increases the flexibility of the inner tubular portion; and at least one electrical element in electrical connection with the inner coil conductor, the at least one electrical element configured to deliver electrical energy to tissue, wherein the inner tubular portion is rotatable relative to the outer tubular portion and the inner tubular portion is less stiff relative to the outer tubular portion along the curved section such that the curved shape is substantially maintained when the inner tubular portion is rotated relative to the outer tubular portion.

In example 14, the lead of example 13, wherein the inner tubular portion is stiffer along the proximal section than along the curved portion.

In example 15, the lead of either of examples 13 or 14, wherein: the inner tubular portion comprises a polymer coating on the inner coil conductor along the proximal section; the polymer coating does not extend along the curved section; and the inner polymer jacket does not extend along the proximal section.

In example 16, the lead of any of examples 13-15, wherein the inner coil conductor has a steeper filar pitch along the curved section than along the proximal section.

In example 17, the lead of any of examples 13-16, wherein the inner polymer jacket is a tube and the inner coil conductor can move within the tube.

In example, 18, the lead of any of examples 13-17, further comprising an active fixation mechanism, the active fixation mechanism comprising a housing, an inner coupling located within the housing, and an active fixation element, the housing and the inner coupling having complementary threading and being rotatable relative to each other, the inner coupling connected to the inner tubular portion and the active fixation element, the housing connected to the outer tubular portion, the active fixation mechanism configured such that rotation of the inner tubular portion relative to the outer tubular portion extends and rotates the active fixation element for tissue fixation.

Example 19 concerns an implantable lead having a proximal section, a distal section, and a curved section between the proximal section and the distal section, the implantable lead comprising: a outer tubular portion extending from the proximal section to the distal section, the outer tubular portion defining an exterior surface of the implantable lead, the outer tubular portion having a bias such that the implantable lead assumes a curved shape along the curved section; an inner tubular portion extending within the outer tubular portion, the inner tubular portion comprising an inner coil conductor and an inner polymer jacket over the inner coil conductor along the curved section, the inner tubular member stiffer along the proximal section than the curved section, the outer tubular portion stiffer along the curved section relative to the inner tubular portion along the curved section such that the inner tubular portion can rotate relative to the outer tubular portion while the curved shape is substantially maintained; and an active fixation element on the distal end, the active fixation element in electrical connection with the inner coil conductor and configured to deliver electrical energy to tissue, the fixation element configured to affix to tissue by rotation of the inner tubular portion relative to the outer tubular member.

In example 20, the lead of example 19, wherein each of the inner tubular portion and the outer tubular portion are biased to assume a straight shape along the proximal section.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the subject matter of this disclosure is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
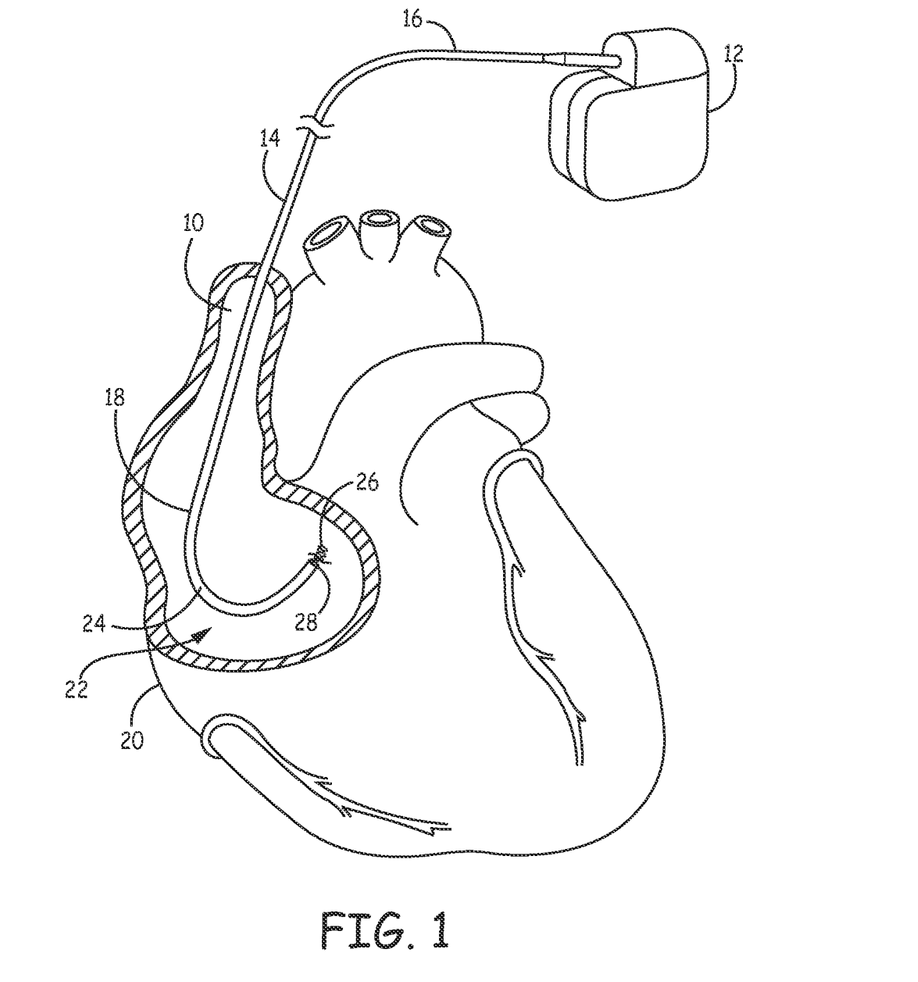
FIG. 1 shows a schematic drawing of a cardiac rhythm management system.

FIG. 1 is a schematic drawing of a cardiac rhythm management system including a pulse generator 12 coupled to a lead 14 having a proximal end 16 and a distal end 18. The pulse generator 12 can be implanted within a pocket formed in the patient's chest or abdomen. In various embodiments, the pulse generator 12 can be a pacemaker, an implantable cardiac defibrillator, and/or include both pacing and defibrillation capabilities. While the pulse generator 12 and lead 14 of FIG. 1 are configured and arranged for delivering cardiac therapy, various pulse generators and leads of the present disclosure may be configured and implanted for sensing bioelectrical activity and/or delivering electrical stimulus to various other targets within the patient.

The lead 14 can enter the vascular system through a vascular entry site formed in the wall of the left subclavian vein (not illustrated) and extend through the left brachiocephalic vein (not illustrated) and the superior vena cava 10 to access the patient's heart 20. In the embodiment illustrated in FIG. 1, the distal end 18 of the lead 14 extends into the right atrium 22 and is anchored by active fixation element 26 that penetrates a wall of the right atrium 22. The active fixation element 26 can be a fixation helix configured to be screwed into tissue to chronically anchor the distal end 18 of the lead 14. The active fixation element 26 can be electrically conductive for sensing and/or delivering stimulation at the anchor location. The distal end 18 of the lead 14 can have a bias to form the preformed curve 24. The preformed curve 24 can allow the lead 14 to curve around to engage the atrial wall (e.g., proximate the bundle of His) after extending down the superior vena cava 10. The preformed curve 24 can allow the lead 14 to have minimal stress within the lead 14 because the lead 14 is biased to assume a shape that fits at least part of the implant arrangement. For example, the components of the distal end 18 of the lead 14 may not resist, or may only minimally resist, being placed along the curved path of the lead 14 shown in FIG. 1. Additionally, the preformed curve 24 can minimize the amount that the active fixation element 26 might have to pull on the tissue of the atrial wall to keep the lead 14 anchored.

Figure 2:
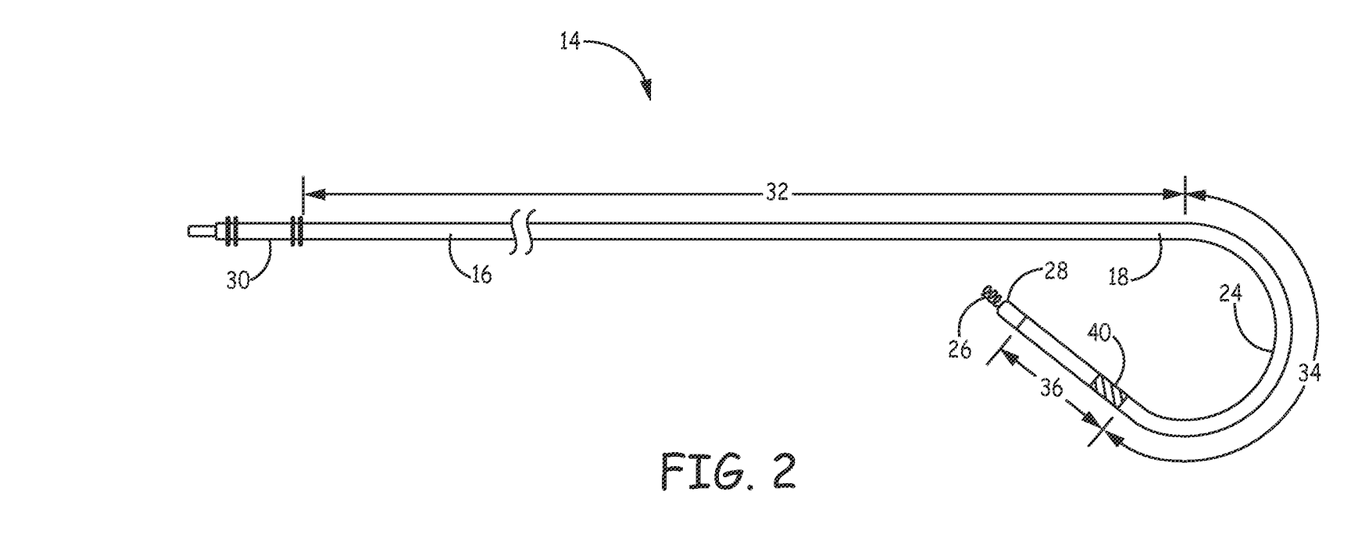
FIG. 2 shows a schematic drawing of an implantable lead.

FIG. 2 illustrates a schematic view of the lead 14. The lead 14 can be biased to assume the shape shown in FIG. 2. In particular, the lead 14 can be biased to assume different shapes along multiple sections of the lead. For example, the proximal section 32 of the lead 14 can be biased to assume a straight shape, the curved section 34 can be biased to assume the preformed curve 24, and/or the distal section 36 can be biased to assume a straight shape. The overall shape of the lead 14 in FIG. 2 can be referred to as a J shape. As will be further discussed herein, the components of the lead 14 forming each of the proximal section 32, the curved section 34, and/or the distal section 36 can have mechanical biases to assume particular shapes. The aggregate mechanical biases of the components of each section can determine the overall shape of the section.

It is noted that even though the proximal section 32, the curved section 34, and/or the distal section 36 can each be biased to assume particular shapes, each section can nevertheless be flexible such that a force placed on the section can overcome the bias of the section to deform the section from the shape it otherwise assumes. In various embodiments, part or all of the proximal section 32 and/or part or all of the distal section 36 can be unbiased such that the section does not have a tendency to assume any particular shape (i.e. the section is fully compliant).

The lead 14 can include a proximal connector 30 configured to plug into the pulse generator 12 and/or an intermediate extension (not illustrated) to make a mechanical and electrical connection with the pulse generator 12. The distal end 18 can include an electrode 40. The electrode 40, the active fixation element 26, and/or any other electrical element on the lead 14 can connect with respective conductors extending within the lead 14 to electrically connect with one or more channels of the pulse generator 12. The electrode 40, the active fixation element 26, and/or any other electrical element on the lead 14 can be configured for sensing bioelectrical signals and/or delivering stimulation energy. The electrode 40 can be a ring electrode. Alternative and/or additional electrodes can be provided along the lead 14 for sensing and/or stimulation.

Figure 3:
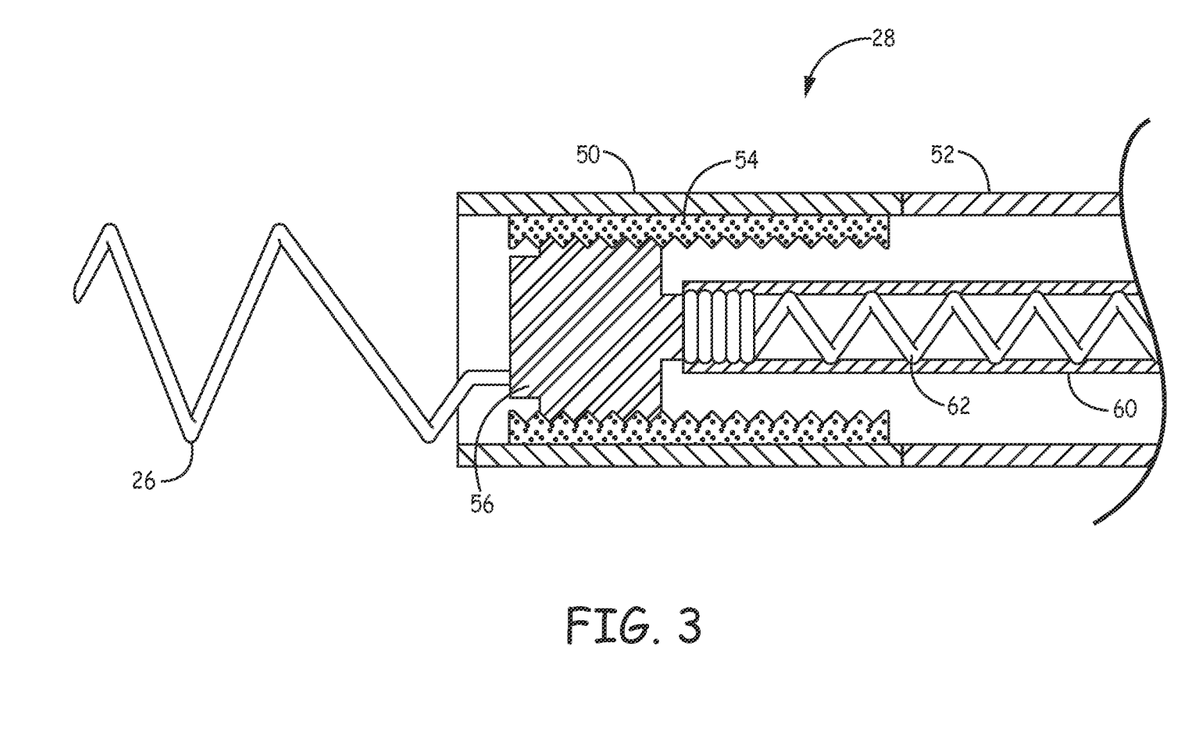
FIG. 3 shows a cross sectional drawing of an active fixation mechanism of an implantable lead.

FIG. 3 shows a cross sectional view of the distal tip 28 of the lead 14. In particular, FIG. 3 shows an active fixation mechanism on the distal tip 28. As shown, the active fixation mechanism comprises a housing 50, a fixation element 26, and an inner coupling 56. The housing 50 can be formed from metal material and/or polymer material such as polyether ether ketone (PEEK). A proximal end of the housing 50 can be attached to a distal end of a polymer tube 52. The polymer tube 52 can define an exterior surface of the lead 14 and can be formed from, for example, silicone or another material. The housing 50 can have an inner surface defining a circular interior. The housing 50 can have threading 54 along the inner surface. The inner coupling 56 can be contained within the circular interior of the housing 50. The inner coupling 56 can be made from conductive metal. A distal end of the inner coupling 56 can be rigidly attached (e.g., via welding) to the active fixation element 26. The inner coupling 56 can include threading on an exterior surface of the inner coupling 56 that is complementary to the threading 54 of the housing 50 such that the inner coupling 56 can be advanced and/or retracted within the housing 50 by relative rotation between the inner coupling 56 and the housing 50. Such advancement of the inner coupling 56 can extend the active fixation element 26 from within the housing 50. Rotation of the inner coupling 56 can rotate the active fixation element 26 to screw the active fixation element 26 into tissue.

A proximal end of the inner coupling 56 can be rigidly attached to an inner coil conductor 62. For example, the inner coupling 56 can include a proximal projection dimensioned to fit within the lumen of the inner coil conductor 62. The inner coil conductor 62 can additionally or alternatively be welded to the inner coupling 56. The inner coil conductor 62 can electrically connect with a contact on the proximal connector 30. In this way, electrical signals can be conducted between the pulse generator 12 and the active fixation element 26 via the inner coil conductor 62 and the inner coupling 56. Further intermediary conductors can be included. In various embodiments, the inner coil conductor 62 can have a single filar which may have low heating advantages in an MRI environment.

The inner coil conductor 62 can extend along the lead 14 from the proximal connector 30 through the distal tip 28. Because the inner coil conductor 62 can extend along the proximal section 32, the curved section 34, and the distal section 36 of the lead 14, the inner coil conductor 62 can be divided into sections which correspond to the proximal section 32, the curved section 34, and the distal section 36. The inner coil conductor 62 can have different mechanical properties along the proximal section 32, the curved section 34, and the distal section 36, as will be further described herein.

As discussed herein, relative rotation between the inner coupling 56 and the housing 50 can extend and rotate the fixation element 26. Being that the fixation of the active fixation element 26 into tissue will occur remote from the clinician (i.e. within the patient's body), the inner coupling 56 and the housing 50 may be required to be stabilized relative to one another such that one of the inner coupling 56 or the housing 50 can be rotated. The polymer tube 52 can stabilize the housing 50 by resisting rotation of the housing 50 by accepting torque from the housing 50. The inner coil conductor 62 can rotate the inner coupling 56 by transferring torque to the inner coupling 56 or stabilize the inner coupling 56 by resisting rotation of the inner coupling 56 by accepting torque from the inner coupling 56. In some embodiments, the inner coil conductor 62 can include an inner polymer jacket 60, discussed further herein, which can in conjunction with the inner coil conductor 62 rotate the inner coupling 56 by transferring torque to the inner coupling 56 or stabilize the inner coupling 56 by resisting rotation of the inner coupling 56 by accepting torque from the inner coupling 56.

The polymer tube 52 may be a part of an outer tubular portion that extends from the proximal connector 30 to the distal tip 28, even though the polymer tube 52 may not extend the entire length of the lead 14. Likewise, either of both the inner coil conductor 62 and the inner polymer jacket 60 may not extend along the entire length of the lead 14, but may be a part of an inner tubular portion that extends from the proximal connector 30 to the distal tip 28. The components of the outer tubular member, such as the polymer tube 52, can be attached to one another such that they can control rotation of the housing 50 from the proximal end 16 of the lead 14. Likewise, the components of the inner tubular member, such as the inner coil conductor 62 and the inner polymer jacket 60, can be attached to one another such that they can control rotation of the inner coupling 56 and the active fixation element 26 from the proximal end 16 of the lead 14. The outer tubular portion and the inner tubular portion are further described in connection with FIGS. 4A-5B.

Figure 4A:
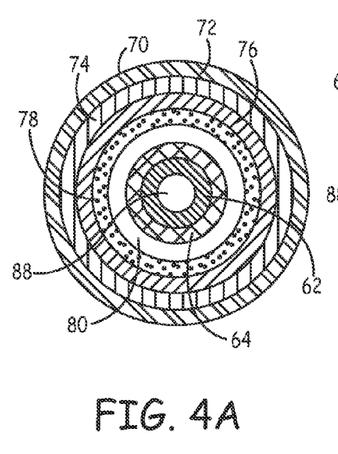
FIGS. 4A-B show cross sectional drawings of an implantable lead.
Figure 4B:
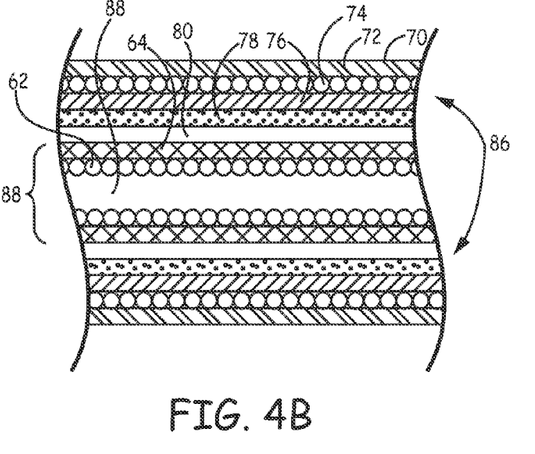
Figure 5A:
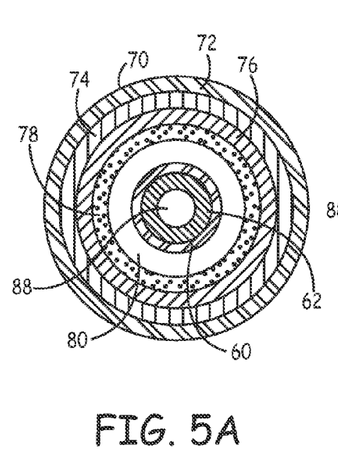
FIGS. 5A-B show cross sectional drawings of an implantable lead.
Figure 5B:
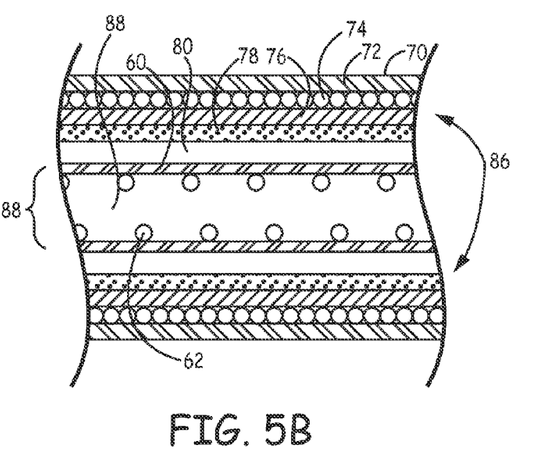

FIGS. 4A-B show cross sectional views of the lead 14 at a location along the proximal section 32. FIGS. 5A-B show cross sectional views of the lead 14 at a location along the curved section 34. FIGS. 4A-B show that the lead 14 can be composed of an outer tubular portion 86 and an inner tubular portion 88 along the proximal section 32. The inner tubular portion 88 and the outer tubular portion 86 are separated by space 80 to allow relative rotation. In some embodiments, one or more polymer tubes and/or other components may be provided along the space 80 between the inner tubular portion 88 and the outer tubular portion 86.

A proximal end of the outer tubular portion 86 can be rigidly connected to a terminal ring (not illustrated) of the proximal connector 30. The terminal ring can rotate relative to other components of the proximal connector 30. The terminal ring can stabilize the outer tubular portion 86 by being kept from rotating (e.g., can be held in place) while the inner tubular portion 88 is rotated. A pin (not illustrated) on the proximal connector 30 can be rotated to rotate the inner tubular portion 88.

The outer tubular portion 86 can include an outer polymer jacket 72 that defines an exterior surface 70 of the lead 14. In some embodiments, the outer polymer jacket 72 can be a polyurethane tube. The type of material forming the outer polymer jacket 72 can change along the length of the lead 14. For example, the outer polymer jacket 72 may be a polyurethane tube along the proximal section and the curved section 34, and may transition to be a silicone tube along the distal section 36 (e.g., the outer polymer jacket 72 of FIGS. 4A-5B may transition to the polymer tube 52 of FIG. 3). The outer tubular portion 86 can include an outer coil conductor 74. The outer coil conductor 74 can be a unifilar coil or can be composed of multiple filars (e.g., 3 or 4 filars). The one or more filars of the outer coil conductor 74 can be individually insulated in some embodiments, although such individual insulation is not shown in FIGS. 4A-5B. The outer coil conductor 74 can conduct electrical signals between the proximal connector 30 and an electrical element on the distal end 18 of the lead 14, such as the electrode 40. In some cases, the outer polymer jacket 72 is heated over the outer coil conductor 74 during assembly to allow the outer polymer jacket 72 to at least partially flow over the filars of the outer coil conductor 74. In this or another way, the outer coil conductor 74 may be mechanically fixed to the outer polymer jacket 72. However, in some other embodiments the outer polymer jacket 72 and the outer coil conductor 74 are not directly mechanically coupled to each other, such that each of the outer polymer jacket 72 and the outer coil conductor 74 can have some degree of relative movement but can still move together when the outer tubular portion 86 is rotated.

The outer tubular portion 86 can comprise an insulating layer 76. The insulating layer 76 may be formed from silicone. The insulating layer 76 may, among other things, provide electrical insulation between the outer coil conductor 74 and the inner conductor coil 62.

The outer tubular portion 86 can also comprise a liner 78. The liner 78 can be formed from a lubricious polymer, such as polytetrafluoroethylene (PTFE). The liner 78 can define an inner lumen of the outer tubular portion 86 inside of which can extend the inner tubular portion 88. The lubricious properties of the liner 78 can reduce friction resulting from engagement between the outer tubular portion 86 and the inner tubular portion 88 during relative rotation.

Although the outer tubular portion 86 is illustrated in FIGS. 4A-5B as being composed of the outer polymer jacket 72, the outer coil conductor 74, the insulating layer 76, and the liner 78, the outer tubular portion 86 can be composed by fewer, additional, and/or alternative components in various embodiments. For example, the outer tubular portion 86 may be composed of only the outer polymer jacket 72 and the outer coil conductor 74 in some embodiments. Moreover, some components may not extend for the entire length of the outer tubular portion 86, such as the outer coil conductor 74, the insulating layer 76, and/or the liner 78. The components of the outer tubular portion 86 can be loosely or tightly connected to one another as a single body such that that torque on one end of the outer tubular portion 86 can rotate the opposing end.

The mechanical properties of the inner tubular portion 88 can change along its length. For example, the inner tubular portion 88 may be relatively stiff along the proximal section 32 and relatively flexible along the curved section 34. Greater flexibility along the curved section 34 can allow the inner tubular portion 88 to be rotated relative to the outer tubular portion 86 while the curve 24 of the curved section 32 is maintained. The inner tubular portion 88 can have different configurations (e.g., different materials and/or modifications to the materials) along the proximal section 32, the curved section 34, and the distal section 36 to provide the differences in mechanical properties, as further discussed herein.

The inner tubular portion 88 can include a polymer coating 64 over the inner coil conductor 62 along the proximal section 32 (as shown in FIGS. 4A-B) and an inner polymer jacket 60 over the inner coil conductor 62 along the curved section 34 (as shown in FIGS. 5A-B). The polymer coating 64 can be stiffer relative to the inner polymer jacket 60. The inner polymer jacket 60 can have a thinner wall relative to the polymer coating 64. A plurality of slots can be formed in the wall of the inner polymer jacket 60 to decrease the stiffness of the inner polymer jacket 60. In some embodiments, the inner polymer jacket 60 may fit more loosely over the inner coil conductor 62 than the polymer coating 64. The polymer coating 64 can be tightly integrated around and between the filars of the inner coil conductor 62.

In some cases, either of the polymer coating 64 or the inner polymer jacket 60 can extend over the inner coil conductor 62 along the distal section 36. The inner polymer jacket 60 and/or the polymer coating 64 can be formed from any of polyamide (e.g., Nylon), polyether block amide (PEBA), polyphthalamide (PPA), ethylene tetrafluoroethylene ETFE, PTFE, and/or other polymer material. The inner polymer jacket 60 can be a disposed over the inner coil conductor 62 as a coating or a tube. Although the inner tubular portion 88 is illustrated as being composed of the inner polymer jacket 60 and the inner coil conductor 62, the inner tubular portion 88 can be composed of additional or alternative components in various embodiments. For example, one or more additional layers of polymer material can be provided along the inner tubular portion 88, such as a layer extending within the lumen of the inner coil conductor 62. The components of the inner tubular portion 88 can be loosely or tightly connected to one another as a single body such that that torque on one end of the inner tubular portion 88 can rotate the opposing end.

The inner tubular portion 88 and the outer tubular portion 86 can transfer opposing torque along the lead 14 from the proximal connector 30 to the distal tip 28 to extend and rotate the active fixation element 26. However, the preformed curve 24 of the curved section 34 can frustrate relative movement of the inner tubular portion 88 and the outer tubular portion 86. Specifically, if the inner tubular portion 88 and the outer tubular portion 86 defining the J-shape of the lead 14 must rotate relative to one another, then one of the inner tubular portion 88 and the outer tubular portion 86 must yield to the other during relative rotation, otherwise the shape of the preformed curve 24 may not be maintained. For example, the distal tip 28 may deflect widely as one curve would twist inside of another curve. Accurate placement of the active fixation element 26 at a target site would be difficult if the shape of the preformed curve 24 is not substantially maintained during extension and rotation.

Various embodiments of the present disclosure concern various configurations of the inner tubular portion 88 and the outer tubular portion 86 to allow relative rotation while substantially maintaining the preformed curve 24 of the curved section 34 (or other shape). In various embodiments, one of the inner tubular portion 88 and the outer tubular portion 86 can be biased to assume the shape of the preformed curve 24 while the other can be stiff enough to transfer torque yet flexible enough to yield to the bias shape of the other tubular portion. For example, in some embodiments, the outer tubular portion 86 is biased such that the lead 14 assumes the shape of the preformed curve 24 along the curved section 34 while the inner tubular portion 88 does not assume a bias shape (e.g., is fully compliant) along the curved section 34. However, the inner tubular portion 88 can still be stiff enough to transfer torque along the lead 14 to extend and rotate the active fixation element 26. In some embodiments, the outer tubular portion 86 and the inner tubular portion 88 can each be biased along the proximal section 32 such that the lead 14 assumes the straight shape of the proximal section 32 while the inner tubular portion 88 may not be biased along the curved section 34 to assume the preformed curve 24. In this way, the inner tubular portion 88 can have variable stiffness along its length.

In various embodiments, any component of the outer tubular portion 86 can be configured to have mechanical bias to assume a particular shape such that the outer tubular portion 86 assumes the shape of the lead 14 along the proximal section 32, the curved section 34, and/or the distal section 36. For example, the outer polymer jacket 72, the insulating layer 76, and/or the liner 78 may be heat set to assume a straight shape along the proximal section 32 and/or a curved shape along the curved section 34. Other polymer and/or metal components of the outer tubular portion 86 can also be biased to assume these or other shapes.

The inner tubular portion 88 may contact the outer tubular portion 86 along the length of the lead 14 in various embodiments. This contact can create friction resistant to rotation of the inner tubular portion 88 relative to the outer tubular portion 86. In some instances, the friction can be additive such that the proximal end of the inner tubular portion 88 must transmit enough torque to overcome the friction along the proximal section 32, the curved section 34, the distal section 36, as well as overcome the friction within the active fixation mechanism. However, the inner tubular portion 88 along the curved section 34 may only have to transmit enough torque to overcome the friction in the curved section 34, the distal section 36, and the active fixation mechanism. Accordingly, the inner tubular portion 88 can be relatively stiffer along the proximal section 32 than along the curved section 34. The polymer coating 64 along the proximal section 32 can stiffen the inner tubular portion 88, however the polymer coating 64 may make the inner tubular portion 88 along the proximal section 34 too stiff to rotate within the outer tubular portion 86 while substantially maintaining the preformed curve 24. Accordingly, in some embodiments, the polymer coating 64 may not be over the inner coil conductor 62 along the curved section 34. In some embodiments, the polymer jacket 60, which can be more flexible relative to the polymer coating 64, can extend over the inner coil conductor 62 along the curved section 34. In some embodiments, a plurality of slots can be formed in the wall of the polymer jacket 60 to increase the flexibility of the polymer jacket 60.

In some embodiments, the mechanical properties of the inner tubular portion 88 can transition along its length (e.g., between the proximal section 32, the curved section 34, and/or the distal section 36). For example, inner tubular portion 88 can be stiffer along the proximal section 32 relative to either or both of the curved section 34 and the distal section 36. The material type, thickness, and/or provision of different features of the inner tubular portion 88 along the proximal section 32 may be different from the material type, thickness, and/or provision of different features of the inner tubular portion 88 along the curved section 32. In some cases, the polymer coating 64 can extend along the proximal section 32 but not along the curved section 34 while the inner polymer jacket 60 can extend along the curved section 34 but not along proximal section 32. In some embodiments, the inner polymer jacket 60 may be bonded to the polymer coating 64. In such cases, the polymer coating 64 can be biased to assume a particular shape while the inner polymer jacket 60 may not be biased to assume a particular shape.

The inner coil conductor 62 can be straight during the coating process (e.g., extrusion), such that the polymer coating 64 heat sets to have a straight mechanical bias. The polymer coating 64 can then be stripped along a section of the inner coil conductor 62 that will extend along the curved section 34 of the lead 14. Removal of the polymer coating 64 can significantly increase the flexibility of the inner tubular portion 88, but may leave the inner coil conductor 62 insufficiently stiff to transfer enough torque along the lead 14 to overcome any friction opposing rotation and/or rotate the active fixation element 26 into tissue in some embodiments.

Several features can stiffen the inner coil conductor 62 along the curved section 34 to permit sufficient torque transfer. For example, the inner coil conductor 62 can be longitudinally stretched. The pitch of the filar pitch can be proportional to the stiffness of a coil, where a higher pitch corresponds to a stiffer coil and a lower pitch corresponds to a less stiff coil. Longitudinally stretching the inner coil conductor 62 along a particular section, such as along the section where the coating was removed, can increase the pitch of the filars along the section and consequently stiffen the section.

Figure 6:
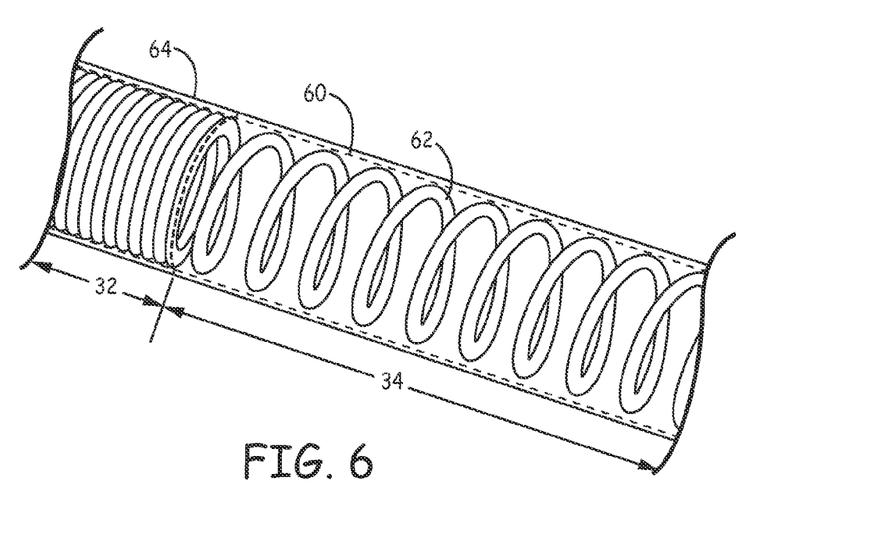
FIG. 6 shows a coil conductor within a polymer jacket.

FIG. 6 shows a schematic view of the polymer coating 64 and the inner polymer jacket 60 along the inner coil conductor 62 at the transition from the proximal section 32 to the curved section 34 (e.g., in isolation from other components of the lead 14). Following removal of the polymer coating 64 from the inner coil conductor 62 along the curved section 34, the inner coil conductor 62 can be longitudinally stretched along the curved section 34. In some embodiments, the inner coil conductor 62 can also be longitudinally stretched along the distal section 36, as shown in FIG. 3. In some cases, the filars of an unstretched section (e.g., along the proximal section 32) can be arranged such that each filar turn contacts adjacent filar turns, which is referred to herein as a closed filar pitch. The filars of a longitudinally stretched section can be separated such that the filar of each turn does not contact the turns of adjacent filars, which is referred to herein as an open filar pitch. A section of closed filar pitch has a higher turns-per-unit-length measure (e.g., turns per inch) than a section of open filar pitch. For example, a closed filar pitch section can have about 4 times as many turns per unit length as an open filar pitch section.

In some embodiments, the polymer coating 64 can be applied over the full length of the inner coil conductor 62. The polymer coating 64 can then be stripped away from the curved section 34 but left in place along the proximal section 32 and the distal section 36. The inner coil conductor 62 can then be longitudinally stretched along the curved section 34. In some embodiments, no additional polymer is provided directly over the longitudinally stretched inner coil conductor 62. However, in some other embodiments, the inner polymer jacket 60 is provided directly over the stretched inner coil conductor 62, replacing the stripped polymer coating. In some embodiments, the inner polymer jacket 60 can be provided as a tube that is slid over the curved section 34 of the inner coil conductor 62. In some cases, the inner coil conductor 62 has a larger outer diameter than the inner diameter of the tube that is slid over the curved section 34. In this case, the inner coil conductor 62 can be twisted or further stretched (below the elastic limit of the inner coil conductor 62) along the curved section 34 to temporarily reduce the outer diameter of the inner coil conductor 62 to allow the tube to be slid over the curved section 34. The inner coil conductor 62 can then be released to allow the outer diameter to radially expand to the inner diameter of the tube.

While an open filar pitch section of a conductor coil may have greater stiffness, the turns of the conductor coil may have a tendency to radially expand and/or unwind when torqued opposite to the filar pitch orientation. For example, if the active fixation element 26 has been screwed into tissue, but the implanting clinician decides to implant the distal tip 28 at a different location, then the inner tubular portion 88 can be turned in the opposite direction in which it was previously turned. However, friction within the lead 14 opposing rotation and/or resistance to unscrewing the active fixation element 26 can result in unwinding and/or radial expansion of the inner coil conductor 62 along where the inner coil conductor 62 is longitudinally expanded (e.g., along the curved section 34), which can be counterproductive to unscrewing and/or can contribute to other issues.

The inner polymer jacket 60 can inhibit the expanded turns of the curved section 34 from unwinding and/or radially expanding beyond the circumference of the inner polymer jacket 60. For example, if a clinician is turning the inner tubular portion 88 to back the active fixation element 26 out from tissue, and resistance to rotation along the inner coil conductor 62 urges the turns to radially expand, then the inner polymer jacket 60 can resist radial expansion of the inner coil conductor 62 along the curved section 34. Provision of the inner polymer jacket 60 along the inner coil conductor 62 can also stiffen the inner tubular portion 88 along the curved section 34 to facilitate greater torque transfer.

In some cases, the inner polymer jacket 60 along the curved section 34 can be a tube that is not extruded over the inner coil conductor 62, and is accordingly not heat set over the inner coil conductor 62 to take a particular shape (e.g., as opposed to extrusion or heat shrinking processes). The material forming the inner polymer jacket 60 along the curved section 34 can be of a different type than the material forming the inner polymer jacket 60 along the proximal section 32. For example, the polymer coating 64 along the proximal section 32 may be stiffer than the inner polymer jacket 60 along the curved section 34. Either of the polymer coating 64 and the inner polymer jacket 60 can be disposed over the inner coil conductor 62 by extrusion or heat shrink. In some cases, the inner polymer jacket 60 along the curved section 34 can have a different thickness than the polymer coating 64 along the proximal section 32. For example, the polymer coating 64 can be thicker than the inner polymer jacket 60. In some embodiments, the inner polymer jacket 60 has a thickness of about 0.001 inches.

Figure 7:
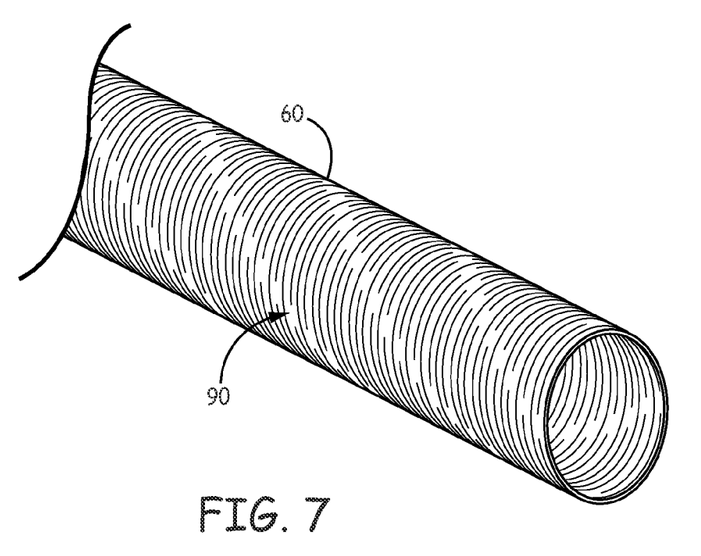
FIG. 7 shows a polymer jacket having a plurality of slots.

FIG. 7 shows a schematic view of an inner polymer jacket 60, according to various embodiments, in isolation from the other components of the lead 14. As shown in FIG. 7, the inner polymer jacket 60 can have a plurality of slots 90. The plurality of slots 90 can be formed within the inner polymer jacket 60 along the curved section 34 to make the inner tubular portion 88 more flexible along the curved section 34. The plurality of slots 90 can be arranged in a variety of patterns. In some embodiments, each slot extends around part of the circumference of the inner polymer jacket 60. In some embodiments, each slot extends orthogonal to the longitudinal axis of the inner polymer jacket 60. Slots oriented in this way can increase the flexibility of the inner polymer jacket 60 and can consequently increase the flexibility of the inner polymer jacket 60 along which the plurality of slots 90 extend. The plurality of slots 90 can be arrayed along the length of the inner polymer jacket 60. The plurality of slots 90 can be equally spaced along the inner polymer jacket 60. As shown in FIG. 7, the plurality of slots 90 can form a winding pattern around the inner polymer jacket 60. As shown in FIG. 7, the ends of alternating slots 90 can be offset by a particular distance or angular degree such that the ends of the slots 90 wind around the inner polymer jacket 60.

A pattern of slots can be formed in the inner polymer jacket 60 by various processes. In some cases, each slot can be mechanically machined from a polymer tube. For example, a spinning wheel can cut or grind each slot. In some cases, each slot can be formed by a laser removing or melting the polymer of each slot. In some embodiments, each slot is about 0.001 inches wide.

In some cases, the inner polymer jacket 60 along the curved section 34 can be the same polymer member as the polymer coating 64 that is applied over inner coil conductor 62 along the proximal section 32. In such cases, the inner polymer jacket 60, in coating form, can be slotted along the curved section 34 to selectively reduce the stiffness of the inner polymer jacket 60 along the curved section 34.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable lead having a proximal section, a distal section, and a curved section between the proximal section and the distal section, the implantable lead comprising:
   an outer tubular portion extending from the proximal section to the distal section, the outer tubular portion defining an exterior surface of the implantable lead, the outer tubular portion having a bias such that the implantable lead assumes a curved shape along the curved section;
   an inner tubular portion extending within the outer tubular portion, the inner tubular portion comprising an inner coil conductor and an inner polymer jacket over the inner coil conductor along the curved section, the inner coil conductor extending from the proximal section to the distal section and having a steeper filar pitch along the curved section than along the proximal section, the inner polymer jacket having a plurality of slots along the curved section that increases the flexibility of the inner tubular portion; and
   an active fixation element on the distal end, the active fixation element in electrical connection with the inner coil conductor, the active fixation element configured to affix to tissue by rotation of the inner tubular portion relative to the outer tubular member.

2. The implantable lead of claim 1, wherein the outer tubular portion is stiffer than the inner tubular portion along the curved section such that the curved shape of the implantable lead is substantially maintained during rotation of the inner tubular portion relative to the outer tubular portion.

3. The implantable lead of claim 1, wherein the inner tubular portion is relatively stiffer along the proximal section and less stiff along the curved portion.

4. The implantable lead of claim 1, wherein the inner polymer jacket inhibits radial expansion of the inner coil conductor during rotation of the inner tubular portion.

5. The implantable lead of claim 1, wherein the inner coil conductor has the same filar pitch along the proximal section and the distal section.

6. The implantable lead of claim 1, wherein:
the inner tubular portion comprises a polymer coating on the inner coil conductor along the proximal section; the polymer coating does not extend along the curved section; and
the inner polymer jacket does not extend over the inner coil conductor along the proximal section.

7. The implantable lead of claim 1, wherein the inner polymer jacket does not extend along the distal section.

8. The implantable lead of claim 1, wherein the inner polymer jacket is a tube and the inner coil conductor can move within the tube.

9. The implantable lead of claim 1, wherein the inner coil conductor is a unifilar coil.

10. The implantable lead of claim 1, further comprising an active fixation mechanism, the active fixation mechanism comprising a housing, an inner coupling located within the housing, and the active fixation element, the housing and the inner coupling having complementary threading and being rotatable relative to each other, the inner coupling connected to the inner tubular portion and the active fixation element, the housing connected to the outer tubular portion, the active fixation mechanism configured such that rotation of the inner tubular portion relative to the outer tubular portion extends and rotates the active fixation element for tissue fixation.

11. The implantable lead of claim 1, comprising a proximal connector configured to interface with an implantable pulse generator, the proximal connector comprising a mechanism that can rotate the inner tubular portion relative to the outer tubular portion, wherein the inner tubular portion and the outer tubular portion are each connected to the proximal connector.

12. The implantable lead of claim 1, wherein the outer portion further comprises a ring electrode and an outer coil conductor, the outer coil conductor electrically connected with the ring electrode.

13. An implantable lead having a proximal section, a distal section, and a curved section between the proximal section and the distal section, the implantable lead comprising:
an outer tubular portion extending from the proximal section to the distal section, the outer tubular portion defining an exterior surface of the implantable lead, the outer tubular portion having a bias such that the implantable lead assumes a curved shape along the curved section;
an inner tubular portion extending within the outer tubular portion, the inner tubular portion comprising an inner coil conductor and an inner polymer jacket over the inner coil conductor along the curved section, the inner coil conductor extending from the proximal section to the distal section, the inner polymer jacket having a plurality of slots along the curved section that increases the flexibility of the inner tubular portion; and
at least one electrical element in electrical connection with the inner coil conductor, the at least one electrical element configured to deliver electrical energy to tissue, wherein the inner tubular portion is rotatable relative to the outer tubular portion and the inner tubular portion is less stiff relative to the outer tubular portion along the curved section such that the curved shape is substantially maintained when the inner tubular portion is rotated relative to the outer tubular portion.

14. The implantable lead of claim 13, wherein the inner tubular portion is stiffer along the proximal section than along the curved portion.

15. The implantable lead of claim 13, wherein:
the inner tubular portion comprises a polymer coating on the inner coil conductor along the proximal section;
the polymer coating does not extend along the curved section; and
the inner polymer jacket does not extend along the proximal section.

16. The implantable lead of claim 13, wherein the inner coil conductor has a steeper filar pitch along the curved section than along the proximal section.

17. The implantable lead of claim 16, wherein the inner polymer jacket is a tube and the inner coil conductor can move within the tube.

18. The implantable lead of claim 13, further comprising an active fixation mechanism, the active fixation mechanism comprising a housing, an inner coupling located within the housing, and an active fixation element, the housing and the inner coupling having complementary threading and being rotatable relative to each other, the inner coupling connected to the inner tubular portion and the active fixation element, the housing connected to the outer tubular portion, the active fixation mechanism configured such that rotation of the inner tubular portion relative to the outer tubular portion extends and rotates the active fixation element for tissue fixation.

19. An implantable lead having a proximal section, a distal section, and a curved section between the proximal section and the distal section, the implantable lead comprising:
a outer tubular portion extending from the proximal section to the distal section, the outer tubular portion defining an exterior surface of the implantable lead, the outer tubular portion having a bias such that the implantable lead assumes a curved shape along the curved section;
an inner tubular portion extending within the outer tubular portion, the inner tubular portion comprising an inner coil conductor and an inner polymer jacket over the inner coil conductor along the curved section, the inner tubular member stiffer along the proximal section than the curved section, the outer tubular portion stiffer along the curved section relative to the inner tubular portion along the curved section such that the inner tubular portion can rotate relative to the outer tubular portion while the curved shape is substantially maintained; and
an active fixation element on the distal end, the active fixation element in electrical connection with the inner coil conductor and configured to deliver electrical energy to tissue, the fixation element configured to affix to tissue by rotation of the inner tubular portion relative to the outer tubular member.

20. The implantable lead of claim 19, wherein each of the inner tubular portion and the outer tubular portion are biased to assume a straight shape along the proximal section.

* * * * *